United States Patent [19]

Muetterties

[11] 4,238,108
[45] Dec. 9, 1980

[54] FLOW CONTROL DEVICE
[75] Inventor: Andrew J. Muetterties, Gages Lake, Ill.
[73] Assignee: Abbott Laboratories, Chicago, Ill.
[21] Appl. No.: 905,305
[22] Filed: May 12, 1978
[51] Int. Cl.³ ............................................... F16K 7/06
[52] U.S. Cl. ..................................... 251/6; 24/115 L
[58] Field of Search ...................... 251/6, 4; 24/115 L

[56] References Cited
U.S. PATENT DOCUMENTS

| | | | |
|---|---|---|---|
| 3,099,429 | 7/1963 | Broman | 251/6 |
| 3,135,259 | 6/1964 | Evans | 251/6 X |
| 3,189,038 | 6/1965 | Von Pechmann | 137/315 |
| 3,685,787 | 8/1972 | Adelberg | 251/6 |
| 3,802,463 | 4/1974 | Dabney | 251/6 X |
| 3,893,468 | 7/1975 | McPhee | 251/6 X |
| 3,918,675 | 11/1975 | Forberg | 251/6 |

Primary Examiner—Martin P. Schwadron
Assistant Examiner—Richard Gerard
Attorney, Agent, or Firm—Robert L. Niblack; Neil E. Hamilton

[57] ABSTRACT

An improved flow control device for regulating the flow of fluid through flexible tubing wherein the flow control device utilizes a rotatable member with trunnions positioned to be captively guided and rotated along guide surfaces. The rotatable member is easily inserted into the clamp body yet once it is placed therein it is difficult to remove without excessive force. The clamp body affords a rigid structure with the opposing walls being fixed at their ends yet are flexible enough to afford entry of the rotatable member into the clamp body for placement of the trunnions in the guide surfaces. In one embodiment, a ramp means is provided through an infeed section wherein the ridge portions forming the ramp merge with the guide surfaces so that when the trunnions of the roller move up the ramp and onto the guide surfaces, an outward flexing of the clamp wall is effected with a retention of the trunnions on the guide surfaces. In another embodiment, the walls defining an open slot at the top of the clamp body are weakened such as by beveling so as to permit the trunnions of the roller to enter into the clamp cavity and be retained on the guide means.

7 Claims, 8 Drawing Figures

U.S. Patent  Dec. 9, 1980  4,238,108
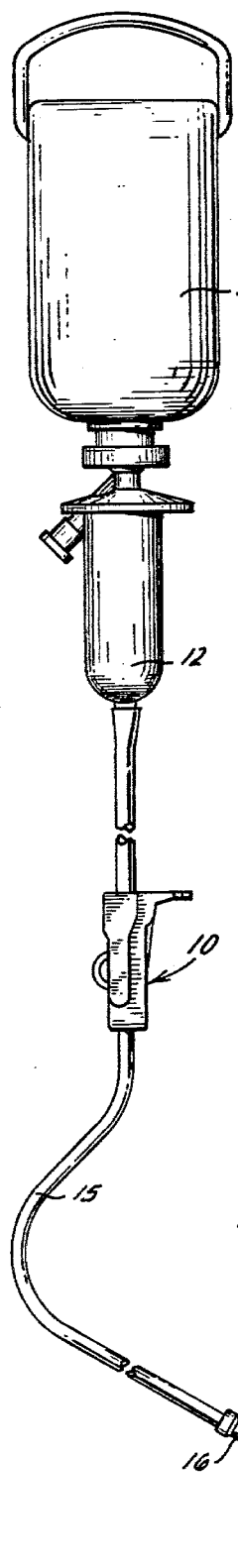
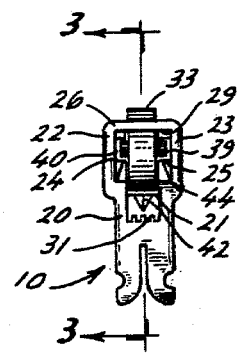
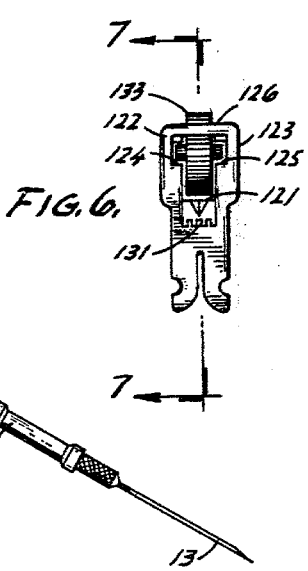
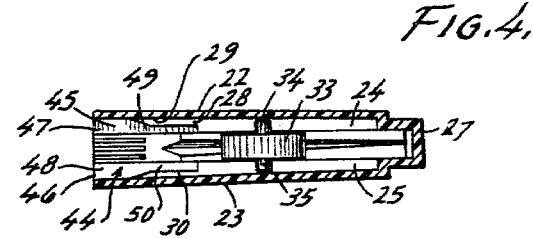
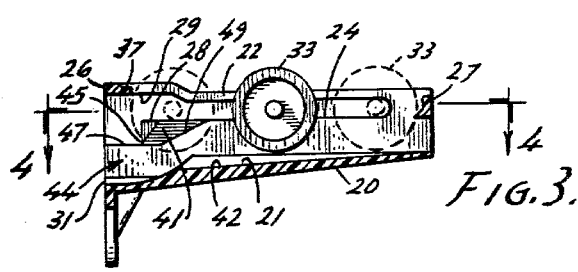
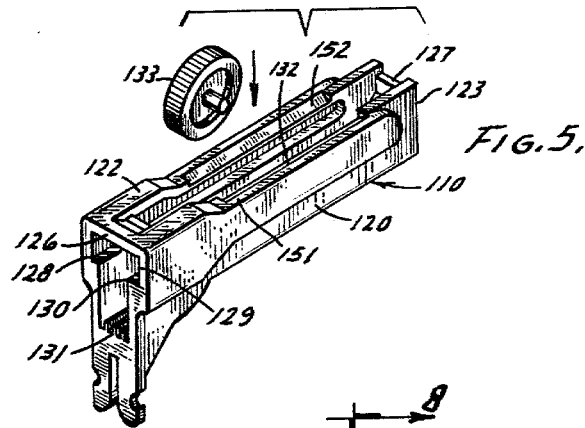
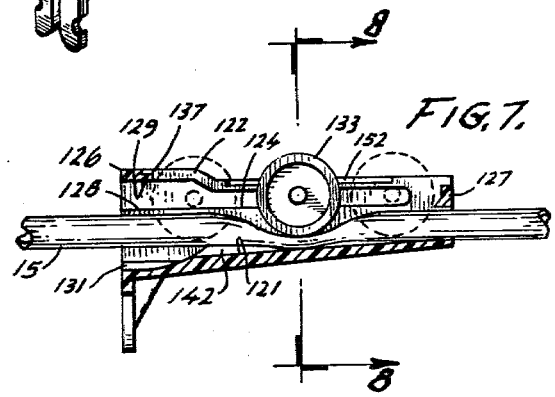
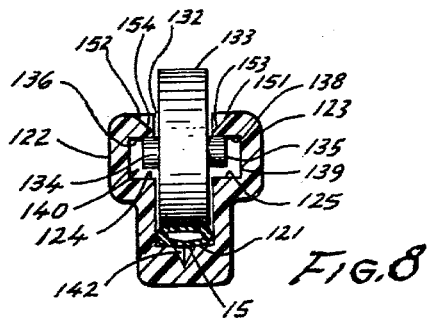

FLOW CONTROL DEVICE

BACKGROUND OF THE INVENTION

This invention relates to an improved flow control unit for accurately controlling the flow of fluid through a length of flexible I.V. tubing. More particularly, this invention relates to a disposable clamp and flow control member utilizing a roller member to exert a controlled force on a length of tubing and in a manner such that the roller member can be easily inserted into the clamp body yet is captively held therein so that unintentional removal of the roller can only be effected with extreme difficulty.

Clamping devices or fluid flow control units of the type concerned with in this invention are disclosed in U.S. Pat. Nos. 3,685,787; 3,802,463; 3,893,468 and 3,918,675. In U.S. Pat. Nos. 3,685,787 and 3,802,463 open end portions of a clamp body are provided for both insertion of the tubing and placement of a roller clamp with trunnions which ride up a ramp means and onto a guide track. However, even with the roller exerting a compressive force on the tubing so as to offer resistance to movement of the roller, the roller can be inadvertently forced to travel a reverse path down the ramp either by movement of the roller directly or indirectly by a pulling action on the tubing in the direction of the open end of the clamp. Obviously, this is an undesirable condition. In U.S. Pat. Nos. 3,893,468 and 3,918,675 stop members are provided along the roller track so as to prevent dislodgment of the roller. However, these stop members can pose problems in inserting the roller into the clamp body in that the roller member must be force fitted past these stop members which may require considerable force. Further, there is the problem that if the stop members are not of sufficient size or dimension they can be easily broken or do not serve their function and permit the trunnions of the roller to pass around or over them.

It is an advantage of the present invention to provide an improved clamp and flow control unit for flexible tubing wherein a rotatable member can be easily positioned inside a clamp body and retained therein in a secure manner even with extensive forces being exerted on the tubing or the rotatable member. Other advantages are a clamp member with a snap-in roller feature which is easily molded yet durable, is disposable and can accurately control the flow of fluid through flexible tubing.

SUMMARY OF THE INVENTION

The foregoing advantages are accomplished and the shortcomings of the prior art are overcome by the improved clamp and flow control member disclosed wherein a clamp body defines a support surface for a length of flexible tubing and opposing walls extend from the support surface to define guide surfaces in the walls. The guide surfaces are spaced from the support surface a predetermined distance and extend substantially in the direction of the longitudinal axis of the clamp body. End wall members interconnect the opposing walls and present an open, slot-like portion to afford an outward flexing of the walls. An open infeed section is also provided in the clamp body for the tubing and extends between the opposing walls and one of the end wall members. The infeed section has a floor portion which is spaced from an end of the support surface, with the floor portion spaced from the guide surfaces at a greater distance than the support surface. A rotatable member having trunnions is positioned and captively guided along the guide surfaces with the guide surfaces presenting an uninterrupted path for the trunnions. In one embodiment, an end wall member is positioned adjacent the open infeed section to provide a stop surface for the rotatable member. In a preferred embodiment, ramp means extend through the infeed section and join the guide surfaces in a coextensive manner and intermediate their ends. In still another embodiment, an open slot between the two walls opposite the support surface of the clamp body has flexible portions to permit the trunnions members to be passed therethrough and into the clamp body.

BRIEF DESCRIPTION OF THE DRAWINGS

A better understanding of the improved clamp and flow control unit of this invention will be accomplished by reference to the drawings wherein:

FIG. 1 is a view in side elevation illustrating the flow control clamp member operatively associated with a parenteral administration unit.

FIG. 2 is an end view of the clamp unit of this invention illustrating the infeed section for the clamp roller and the tubing.

FIG. 3 is a view in vertical section taken along line 3—3 of FIG. 2.

FIG. 4 is a view in horizontal section taken along line 4—4 of FIG. 3.

FIG. 5 is a top perspective view of an alternative embodiment showing the roller member in position prior to placement in the clamp body.

FIG. 6 is a view similar to that of FIG. 2 illustrating an end view of the alternative embodiment shown in FIG. 5.

FIG. 7 is a view in vertical section taken along line 7—7 of FIG. 6.

FIG. 8 is a view in vertical section taken along line 8—8 of FIG. 7.

DESCRIPTION OF THE PREFERRED EMBODIMENT

Proceeding to a detailed description of a preferred embodiment of the present invention, the improved flow control device, generally 10, is shown for use in conjunction with a parenteral administration unit composed of a solution container 11 and a drip chamber 12 which is interconnected to a hypodermic needle 13 by means of a length of tubing 15 connected to needle adapter 16.

As shown in FIGS. 2-4, the improved flow control clamp device 10 includes a clamp body 20 having a rigid support or clamping surface 21 for tubing 15. Extending from the support surface 21 are opposing walls 22 and 23 which contain a pair of guide surfaces 24 and 25, respectively. End walls or ribs 26 and 27 interconnect the opposing walls, with end wall 26 forming in conjunction with opposing walls 22 and 23 an open infeed section 29 for entry of a rotatable member 33, preferably in the form of a roller, as well as tubing 15 into the clamp body. The open infeed section for the roller has a floor portion 31 which is spaced from clamping surface 21 and is spaced from the guide surfaces 24 and 25 a greater distance than is support surface 21. The rotatable member 33 has oppositely disposed trunnions 34 and 35 which ride in the closed tracks 40 and 39 forming guide surfaces 24 and 25, respectively, between opposing walls 22 and 23.

As best seen in FIGS. 3 and 4, a ramp generally 44 is provided in the infeed section 29 and extends from one end of walls 22 and 23. It includes a pair of ridge portions 45 and 46 which extend outwardly from the opposing walls and provide track members terminating adjacent walls 22 and 23. Ridges 45 and 46 are in the form of segments 47 and 48 which are parallel to guide surfaces 24 and 25 but spaced therefrom and interconnected therewith by inclined segments 49 and 50. It will be seen that guide surfaces 24 and 25 have extensions 28 and 30 which extend into the infeed section 29, adjacent the inclined segments 49 and 50 and a portion of parallel segments 47 and 48. It should also be pointed out that except for the joining by end walls 26 and 27 of opposing walls 22 and 23, they are spaced apart to provide an opening for extension of a portion of rotatable member 33 therebetween and outwardly therefrom as will be generally indicated by numeral 132 in embodiment 110 shown in FIG. 5.

ALTERNATIVE EMBODIMENT

FIGS. 5-8 represent an alternative embodiment of the improved flow control device with similar numbers in the "100" series being used to illustrate similar parts as in device 10. The main difference between flow control device 10 and 110 is that in place of the ramp 44 as a means of inserting the roller 133 into the clamp body, flexible portions 151 and 152 are provided along an open slot 132 formed between opposing walls 122 and 123 and end walls 126 and 127. The flexible portions are formed from beveled surfaces 154 and 153 to provide a reduced wall thickness so as to afford a slight flexing of the walls 122 and 123 in this immediate area so as to permit the trunnions 134 and 135 to pass therebetween by means of an outward flexing of the wall portions. This permits the trunnions to enter and be retained in guide tracks 139 and 140. The beveled surfaces are preferably formed at a 45° angle with respect to the horizontal plane of the clamp body.

OPERATION

A better understanding of the advantages of the improved flow control and clamp devices 10 and 110 will be had by a description of their operation. Referring to control device 10 first, the roller 33 will be in an unassembled condition concerning clamp body 20 and outside its confines. Tubing 15 will be fed in through the infeed section 29 placed across floor 31 with channel 42 and also support surface 21 until the tubing extends completely through the clamp body and beyond. Next, roller 33 will be placed over the tubing and also in through the infeed section 29 with rib 26 spaced from floor 31 to permit entry and the trunnions 34 and 35 placed on parallel segments 47 and 48 of ramp 44. Inward motion of the roller will cause the trunnions to ride up the inclined segments 49 and 50 with the trunnions ultimately entering guide surfaces 24 and 25, as best seen in FIG. 4. Once the trunnions contact the guide surfaces 24 and 25, they will remain in contact with them and upon movement of the roller toward the infeed section 29 or end wall 26, they will not ride down inclined segments 49 and 50 but will contact guide surface extensions 28 and 30 of guide surfaces 24 and 25. This is effected by dimensioning of the trunnions 34 and 35 of sufficient distance so that they extend laterally to extensions 28 and 30 when the trunnions are adjacent inclined segments 49 and 50. Accordingly, the roller will remain captive in the clamp body as any movement toward the infeed section will effect contact of the roller with stop surface 37 of wall 26 and at the opposite end by contact with the trunnions 34 and 35 with the end of the guide tracks or with end wall 27. With the roller 33 placed in the clamp body 20, the improved flow control device 10 will have a clamping action similar to that described in U.S. Pat. No. 3,685,787, or as in any other roller clamp wherein an incremental compression of the tubing is effected by a roller member against a support or clamping surface of a clamp body.

The operation of the improved flow control unit 110 will differ from that of unit 10 only in that the loading of the roller member 133 will not be from the open infeed section 129, but instead will be from between the opposing walls 122 and 123 and through the slot 132 opposite the support surface 121. This placement of the roller in the clamp body is effected by forcing the trunnions 134 and 135 over the beveled surfaces 154 and 153 to effect a spreading apart of the opposing walls 122 and 123 until the trunnions seat themselves in guide tracks 139 and 140, as shown in FIG. 8. With the trunnions so seated, the roller is captively held in the clamp body and can move freely along the guide surfaces until the roller either contacts stop surface 137 at one end or the trunnions engage the end of the closed guide tracks 139 and 140 or wall 127, at the opposite end. It will be recognized that with the tubing placed on support surface 121, trunnions will be forced from guide surfaces 124 and 125 and will ride against upper guide surfaces of tracks 140 and 139. The same is true of roller 33 and the placement of trunnions 34 and 35 in tracks 40 and 39 when tubing is present.

An important aspect of this invention is the utilization of a clamp body which has opposing walls such as 22, 23 or 122 and 123 which are rigidly interconnected at their ends such as by end walls 26 and 27 and 126 and 127 yet have sufficient resiliency so that they can be spread apart by contact with the trunnions of the roller members 33 and 133. Concerning embodiment 10, it will be seen in referring to FIG. 4 that ramp segment 49 and extension 28 as well as ramp segment 50 and extension 30 together are of the same width as guide surfaces 24 and 25. It will be further seen that trunnions 34 and 35 extend a distance outwardly from the roller so that they are wider in lateral dimension than inclined segments 49 and 50. Accordingly, when the roller is loaded into the clamp body and over ramp 44, the ends of the trunnions 34 and 35 will laterally contact the opposing walls 22 and 23 in the area adjacent parallel segments 47 and 48 and inclined segments 49 and 50 as indicated by numeral 41, to effect a slight outward movement of the walls to permit the trunnions to move over the inclined segments 49 and 50 until they ultimately are positioned on guide surfaces 24 and 25. Once positioned on guide surfaces 24 and 25 trunnions 34 and 35 will not contact segments 49 and 50 as walls 22 and 23 will have moved inwardly to position trunnions 34 and 35 over them and onto extensions 28 and 30. Referring to FIG. 5, an outward flexing of the opposing walls will be effected as the trunnions 134 and 135 are forced downwardly over the beveled surfaces 154 and 153 to slightly spread the opposing walls apart so that the trunnions can gain entry to the guide tracks 140 and 139. As seen in FIG. 8, trunnions 134 and 135 are of a wider dimension than the slot 132, as formed between the ends of beveled surfaces 153 and 154.

It will be recognized that while the means for captively holding the roller member in the clamp body as well as to gain easy access thereto, is shown in conjunction with a roller clamp wherein the roller maintains a parallel relationship with the clamping surface as described in U.S. Pat. No. 3,685,787, the captive and loading features could also be utilized with any type of a roller clamp having a guide or track means and which could have an intersecting relationship with the clamping floor. As indicated earlier, the opposing walls of the clamp body must be such that they are somewhat rigid in order to effect a controlled clamping relationship between the roller and the tubing yet at the same time must have a degree of flexibility so as to permit the roller to gain entry into the clamping body. Accordingly, the opposing walls as well as the clamping surface and the end walls are molded from a semirigid plastic material, preferably acrylonitrite butadiene styrene (ABS). If desired, other resinous plastic material such as nylon or methyl methacrylate, could be utilized.

It will thus be seen through the present invention that there is now provided an improved flow control unit which affords ready insertion of a roller clamp member yet is captively held therein during its operation. The improved control clamp units afford easy assembly, without extensive or precise molding techniques. At the same time, the roller members are retained captively in the clamp bodies so that even intentional forces directed on the tubing such as a pulling thereof or extensive forces exerted on the roller member against either end of the clamp body will not cause the roller to become disengaged.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A disposable roller-type tubing clamp for regulating flow of fluid through a length of flexible tubing comprising a portion of an intravenous administration set and for preventing the accidental removal of the roller comprising:

a clamp body defining a rigid support surface for said length of flexible tubing, said clamp body having a longitudinal axis;

opposing semiflexible walls extending from said support surface defining opposing track members with guide surfaces integrally disposed in said walls, said guide surfaces spaced from said support surface a predetermined distance and extending substantially in a direction of said longitudinal axis, said opposing walls spaced from each other and presenting an open slot therebetween;

an open infeed section for said tubing defined by said clamp body extending between said walls, said infeed section including a floor portion spaced from an end of said support surface, said floor portion spaced from said guide surfaces a distance greater than said support surface, said guide surfaces extending in at least a portion of said infeed section;

a rotatable member having trunnions positioned to be captively guided and rotated along said guide surfaces with said track members providing confining wall surfaces for the ends of said trunnions; and ridge portions extending inwardly from each end of said opposing walls and defining a substantially transverse supporting ledge surface for said trunnions, said ridge portions spaced a distance away from said guide surfaces at a position where said ridge portions are adjacent said end of said opposing walls in said open infeed section and joining said guide surfaces by inclined surfaces in a continuing manner and intermediate their ends, said trunnions dimensioned to extend transversely over said ridge portions, said inclined and guide surfaces and providing an outward flexing of said walls upon engagement with said inclined surfaces;

so that said rotatable member can be inserted within said clamp body by placement of said trunnions on said ridge portions and upon further movement of said rotatable member into said clamp body said trunnions will move over said ridge portions and said inclined surfaces and onto said guide surfaces upon flexing of said walls and said rotatable member will be retained on said guide surfaces even when positioned adjacent said inclined surfaces.

2. The tubing clamp as defined in claim 1 wherein said guide surfaces are defined by closed walled track members and extend in a generally parallel manner along a major portion of said support surface.

3. The tubing clamp as defined in claim 1 wherein said end wall member adjacent said infeed section defines a generally thin rib member opposite said floor portion.

4. The tubing clamp as defined in claim 3 wherein said rib member in proximity to said open infeed section is spaced a sufficient distance from the floor of said infeed section to permit passage of said rotatable member into said clamp body and positioned from said guide surfaces adjacent said infeed section to provide a stop surface for said rotatable member.

5. The tubing clamp as defined in claim 1 wherein said clamp body includes at least one channel disposed adjacent said support surface.

6. The tubing clamp as defined in claim 1 wherein said ridge portions extend substantially parallel to said guide surfaces and then in a direction to join said guide surfaces.

7. The tubing clamp as defined in claim 1 wherein said rotatable member is defined by a roller.

* * * * *